United States Patent [19]

Marach

[11] Patent Number: 4,741,341
[45] Date of Patent: May 3, 1988

[54] PROTECTION CIRCUIT AND METHOD FOR IMPLANTED ECG TELEMETRY CIRCUITS

[75] Inventor: Ronald R. Marach, Valencia, Calif.

[73] Assignee: Siemens-Pacesetter, Inc., Sylmar, Calif.

[21] Appl. No.: 839,233

[22] Filed: Mar. 12, 1986

[51] Int. Cl.[4] ............................................. A61N 1/36
[52] U.S. Cl. .............................. 128/419 PT; 128/697; 128/903
[58] Field of Search ................ 128/419 PG, 696, 697, 128/903

[56] References Cited

U.S. PATENT DOCUMENTS

| | | | |
|---|---|---|---|
| 4,114,627 | 9/1978 | Lewyn et al. | 128/419 PG |
| 4,228,803 | 10/1980 | Rickards | 128/419 PG |
| 4,300,566 | 11/1981 | Stindt et al. | 128/419 PG |
| 4,506,677 | 3/1985 | Lambert | 128/697 |
| 4,537,201 | 8/1985 | Dellevedove et al. | 128/697 |
| 4,543,955 | 10/1985 | Schroeppel | 128/419 PG |
| 4,558,702 | 12/1985 | Barreras et al. | 128/419 PG |
| 4,567,892 | 2/1986 | Plicchi et al. | 128/419 PG |

Primary Examiner—William E. Kamm
Attorney, Agent, or Firm—Bryant R. Gold

[57] ABSTRACT

A protection circuit for an implanted telemetry circuit used to telemeter ECG or other low level signals sensed on the same lead whereon high level stimulation or other signals may also appear. The protection circuit includes a first FET switch that selectively connects a buffered monitoring point of the lead to the input of the telemetry circuit whenever a telemetry mode of operation is desired. A second FET switch switchably connects the buffered monitoring point to ground in the presence of any high level signals appearing on the lead, thereby preventing such high level signals from being applied to the telemetry circuit.

6 Claims, 2 Drawing Sheets

PROTECTION CIRCUIT AND METHOD FOR IMPLANTED ECG TELEMETRY CIRCUITS

BACKGROUND OF THE INVENTION

The present invention relates to cardiac pacemakers. More particularly, the present invention relates to protecting implanted telemetry or other sensitive circuits within a pacemaker from high level signals, which high level signals could damage or otherwise interfere with the proper operation of the telemetry or other circuits. Even more particularly, the present invention relates to protecting the ECG telemetry circuits of an implanted pacemaker wherein the ECG information to be telemetered is sensed on the same leads used to provide stimulaltion pulses to the heart.

It is known in cardiac pacemaker art to include telemetry circuits within an implanted cardiac pacemaker. Such telemetry circuits allow selected information to be telemetered out of the implanted pacemaker to an external receiver. Early telemetry circuits limited the telemetered information to the status of the pacemaker's circuits, primarily the status of the battery used to power the pacemaker.

In recent years, with the advent of demand-type programmable pacemakers, it has become common to include in the telemetered information from the implanted device the ECG (electrocardiogram) signals sensed by the pacemaker leads that are positioned in one or more chambers of the heart. (It is noted that in a demand-type pacemaker, stimulation pulses are provided to the heart only when the heart does not contract or beat by itself prior to the expiration of a predetermined timed interval. This predetermined timed interval is typically called the escape interval, and it is measured relative to the last or most recent heartbeat or contraction. Where the heart contracts or beats on its own, no stimulation pulses need by generated by the demand pacemaker. This action of not generating stimulation pulses except when needed advantageously conserves power and frees up the pacing lead to function as a sensing lead.)

Further advances in pacemaker art in recent years have significantly reduced the size and weight of implanted pacemakers. Some of this reduction in size has resulted from being able to use smaller batteries. Being able to use smaller batteries, in turn, has been made possible in significant part by the use of highly efficient circuit designs that minimize power consumption.

One circuit configuration that has contributed to efficient circuit design is the use of a positive ground circuit configuration. In a positive ground circuit, all of the circuit potentials are more negative than the reference potential (ground) of the environment in which the circuit is used. In the case of an implanted pacemaker, which typically provides a negative stimulation pulse to the heart, the generation of such a negative stimulation pulse is more efficiently accomplished using a positive ground system. (This efficiency results because most of the circuit components used to generate the negative stimulation pulse remain off—not consuming any power, or very little power—except when the stimulation pulse is generated. Because the stimulation pulse is a narrow low-duty cycle pulse, these components thus remain off most of the time.)

A common element used in a positive ground circuit configuration is a P-channel MOSFET (metal-oxide semiconductor field effect transistor) switch. P-channel MOSFET's, as explained more fully below, remain off unless a negative voltage is applied between the gate and source thereof. (In contrast, an N-channel MOSFET remains off unless a positive voltage is applied between the gate and source.)

It is known in the pacemaker art to use a P-channel MOSFET switch to selectively connect a pacing/sensing lead to an appropriate telemetry circuit. By turning such a switch on during those time periods when the lead is to function as a sensing lead (rather than as a pacing lead), any signals sensed by the lead, such as ECG activity, can be telemetered out of the pacemaker.

When a negative stimulation pulse appears on the pacing/sensing lead, and when all voltages appearing on the pacing/sensing lead are monitored at a buffered monitoring point, a high level positive voltage signal appears immediately subsequent to the negative voltage signal. (This positive-following-negative voltage effect is created in large part by the AC coupling capacitors that must be used in any monitoring circuits within the pacemaker.) Unfortunately, this positive voltage at the source of the P-channel MOSFET switch has the same result as applying a negative voltage to the gate thereof, i.e., the switch is turned on. This turn on allows the positive voltage to be applied to the input of the telemetry circuits. Because this positive voltage typically exceeds the useful and safe operating range of the telemetry circuits, the telemetry circuits may respond by: (1) telemetering meaningless information (noise); (2) becoming saturated to the point where they are inoperable for a significant time period (the recovery period); or (3) at worst, becoming permanently damaged. Hence, there is a need in the art for protecting such telemetry circuits within a pacemaker that are coupled to a pacing/sensing lead through a P-channel MOSFET switch.

SUMMARY OF THE INVENTION

The present invention meets the above-identified need by providing a simple, inexpensive, reliable protection circuit that prevents high level signals from being applied to the telemetry circuits of an implanted pacemaker or similar device. Rather than redesigning the telemetry circuits, or providing sophisticated, power-consuming, front-end protection circuits therefor, which approaches are commonly taken in the art when a similar problem is encountered, the present invention uses an additional P-channel MOSFET switch to ground the telemetry input whenever a positive high level signal may be present.

The invention is thus realized by using, in a positive ground circuit configuration, a first P-channel MOSFET switch to switchably connect a buffered monitoring point of the sensing/pacing lead to the telemetry circuit, as is done in the prior art. In addition, the present invention uses a second P-channel MOSFET switch that connects the buffered monitoring point to ground when a high level positive signal is present at the monitoring point. Such an approach is simple—only requiring one additional element. Further, the approach uses the same type of switch—A P-channel MOSFET switch—that is already being used to interface with the telemetry circuit. This greatly facilitates the overall fabrication of the pacemaker circuits and allows such circuits to be easily implemented in a single chip design.

Further, because this grounding is done on the sensing/pacing lead side of the first switch used to connect the sensing/pacing lead to the telemetry circuit—i.e., at the monitoring point—this configuration offers the additional advantage of causing the desired ground to occur even in the absence of a control signal to turn the second switch on. This is because the second switch desirably turns on for the same reasons that the first switch undesirably turns on whenever a high level positive voltage appears at the monitoring point.

For purposes of the invention described herein, a "high level" signal is any signal having a magnitude that exceeds the safe and useful operating range of a telemetry or other linear-operating type of circuit to which the signal is applied. It follows that a "low level signal" is any signal that falls within the safe and useful operating range of such circuits. To illustrate these definitions, in the preferred embodiment of the present invention, a buffered monitoring point of the pacing/sensing lead is switchably connected through a P-channel MOSFET switch to a voltage controlled oscillator (VCO). This VCO serves as the front end of the telemetry circuit. The VCO is only able to respond to signals in the range of 0–70 mv. Hence, for purposes of this embodiment, a 0–70 mv signal would be considered a low level signal. Similarly, a signal greater than, for example, 100 mv, would be considered a high level signal.

BREIF DESCRIPTION OF THE DRAWINGS

The above and other features and advantages of the present invention will be more apparent from the following more particular description thereof presented in conjunction with the following drawings wherein.

DETAILED DESCRIPTION OF THE INVENTION

Figure 1:
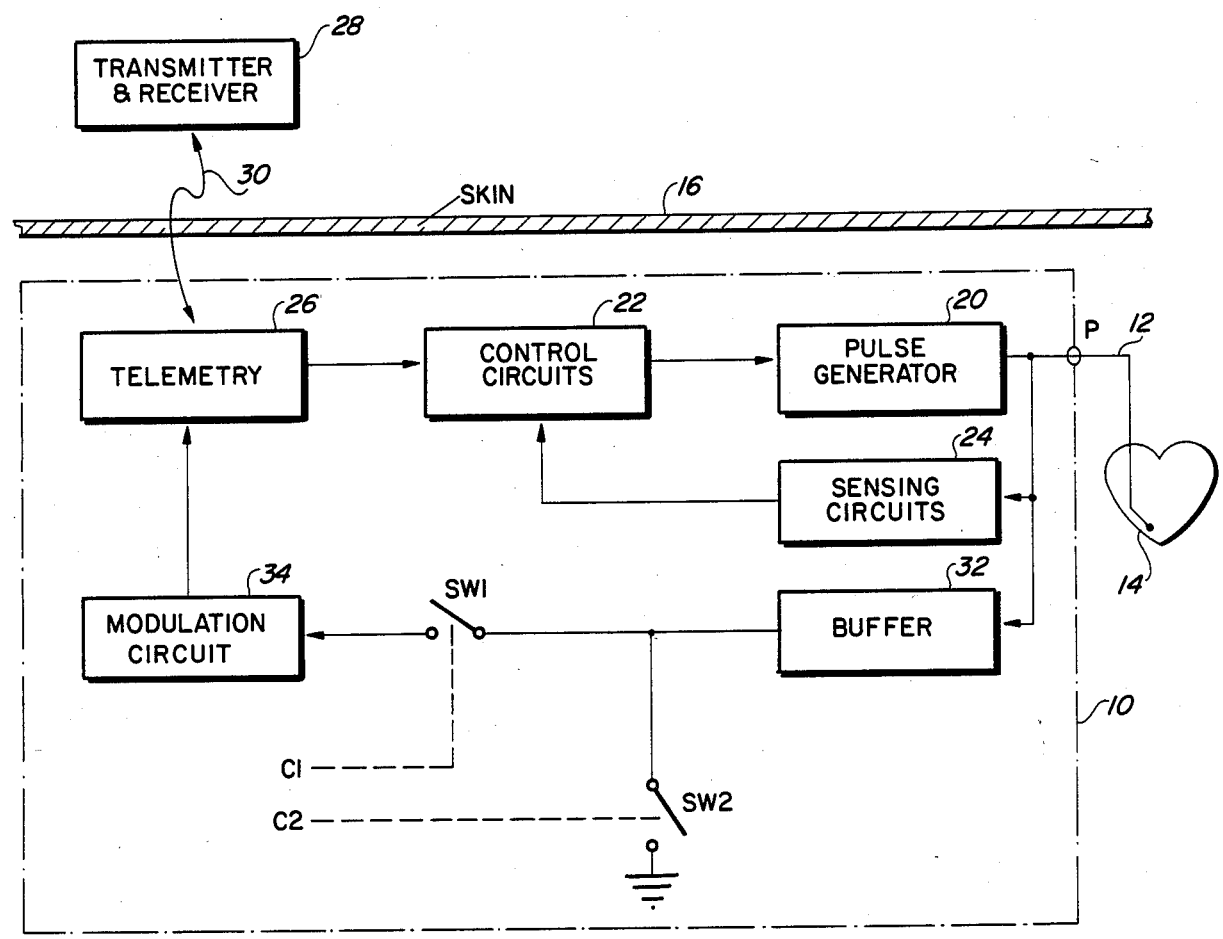
FIG. 1 is a block diagram of an implanted pacemaker, and illustrates the two switches that comprise part of the present invention.

Referring first to FIG. 1, a block diagram of an implanted pacemaker 10 is shown. The pacemaker 10 has at least one pacing/sensing lead 12 that is positioned within a heart 14. The pacemaker 10 is implanted beneath the skin 16 of a patient who uses the pacemaker.

The pacemaker 10 includes a pulse generator 20 that provides stimulation pulses to the pacing sensing lead 12 at appropriate times. The pulse generator 20 is controlled by suitable control circuits 22 that define the various times or intervals within which the heart 14 must naturally contract before a stimulation pulse is provided. Sensing circuits 24 monitor the activity of the heart 14 in order to determine whether the heart 14 has naturally contracted within an appropriate time (i.e., within the escape interval). If such natural contractions occur, then the control circuits 22 disable the pulse generator 20. However, if such natural contractions do not occur, then the pulse generator 20 provides the needed stimulation pulse to the heart.

The control circuits 22 can be programmed to operate in various modes of operation through the implanted telemetry circuits 26 and an external transmitted and receiver 28, as is known and taught in the art. Typically, RF telemetry signals, represented in FIG. 1 as the wavy arrow 30, will be used to establish communication between the external transmitter/receiver 28 and the internal telemetry circuits 26. However, other forms of telemetry are known in the pacemaker art other than RF telemetry. The present invention is applicable to whatever type of telemetry is used.

Still referring to FIG. 1, the pacing/sensing lead 12 is also connected to a buffer circuit 32. The output of the buffer circuit 32 comprises a monitoring point M at which the various signals appearing on the sensing/pacing lead 12 can be monitored without noticeably interfering with the signals that appear on the pacing/sensing lead 12. Said another way, the monitoring point M is isolated from the pacing/sensing lead 12.

The monitoring point M is connected through a first switch SW1 to a modulation circuit 34. The output of the modulation circuit 34 is in turn connected to the implanted telemetry circuits 26. Thus, any signals sensed on the lead 12 can be directed through the buffer circuit 32, the closed switch SW1, to the modulation circuit 34. The modulation circuit 34 can in turn process these signals in order to send appropriate telemetry signals to the external transmitter/receiver 28 through the telemetry circuits 26. In this manner, ECG information sensed on the lead 12 can be telemetered to the external transmitter/receiver 28.

Figure 2:
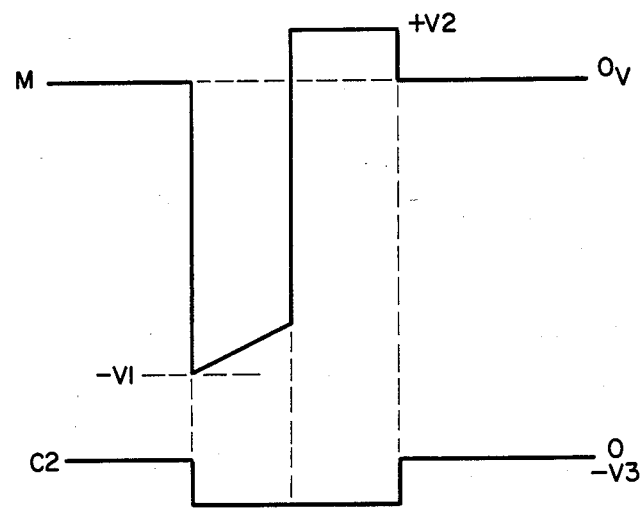
FIG. 2 is a timing diagram illustrating when SW2 of FIG. 1 may be closed, in accordance with one embodiment of the invention, in order to prevent high level signals from reaching the telemetry modulation circuits.

So long as the lead 12 is performing a sensing function, little difficulty is encountered in telemetering the information sensed thereon as described above. However, in a demand-type pacemaker, a stimulation pulse will be generated at appropriate times in order to maintain a desired rhythm of the heart. Such stimulation pulses, as seen at the monitoring point M, appear similar to the waveform shown in FIG. 2. That is, the negative stimulation pulse is first sensed, having a peak of $-V1$ volts. Immediately subsequent to this negative stimulation pulse, a positive pulse of $+V2$ appears. (In a typical pacemaker application, V2 may be on the order of 200 mv.) Typically, whenever such a stimulation pulse is present, the switch SW1 will be opened in order to prevent these high level signals from appearing at the input of the modulation circuit 34. However, as will be explained more fully below, the very presence of such a high level positive signal at point M may cause switch SW1 to close even though the control signal therefore, indicated in FIG. 1 as C1, is attempting to maintain SW1 in an opened position. Hence, in order to prevent the high level signals from being presented to the modulation circuit 34, the present invention includes the addition of switch SW2. This second switch SW2 connects the monitoring point to ground in response to a control signal C2. Typically, the control signal C2 control 5 SW2 as shown in FIG. 2, wherein switch SW2 is closed whenever the C2 signal is negative (at $-V3$ volts in FIG. 2). Thus, in operation, even if a high level signal appears at point M, and even if switch SW1 fails to remain open, switch SW2 closes, thereby grounding point M and preventing the high level signal from appearing at the input of the modulation circuit 34.

Figure 3:
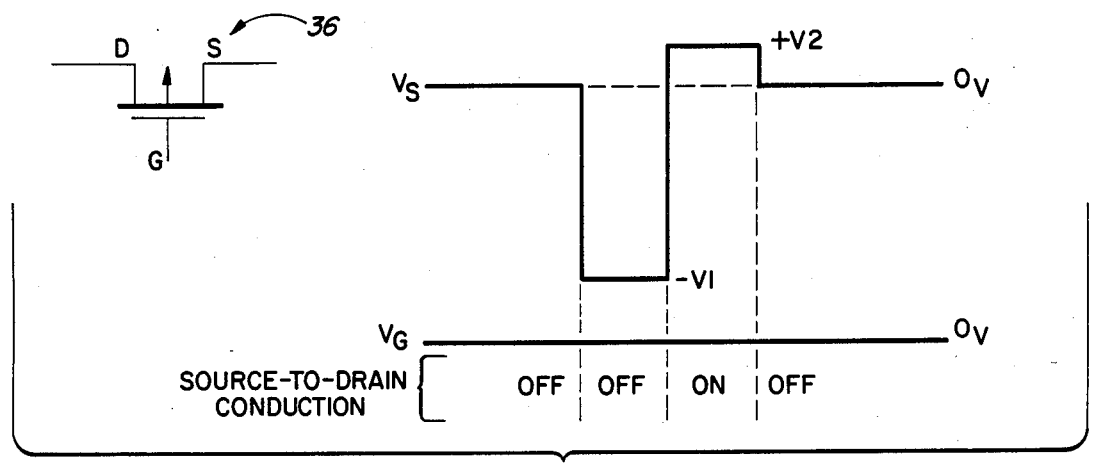
FIG. 3 is a simplified diagram of a P-channel MOSFET switch, illustrating its operation as a switch.

In the preferred embodiment, the switches SW1 and SW2 are realized using P-channel MOSFET devices. Such devices are used because they remain off (or open) in the absence of any applied gate-source signal. To illustrate the operation of a P-channel MOSFET switch, reference is made to FIG. 3 wherein there is shown a schematic representation of a P-channel MOSFET 36, and a timing diagram indicating the status of the source-to-drain conduction of the MOSFET 36 as a function of various voltages applied to the source terminal thereof. As indicated in FIG. 3, the terminals of a MOSFET device are designated as the source S, the drain D, and the gate G. When the MOSFET device is turned on, current can flow between the source and drain (or between the drain and source depending upon the potential applied thereacross). Whether or not current can flow between the source and drain depends upon the voltage applied to the gate (or, more precisely, to the voltage potential between the gate and source). With no voltage applied to the gate, there is no channel between the source and drain through which current can flow. However, the application of a negative voltage to the gate (with respect to the source) causes a channel to be enhanced between the source and drain through which current may flow. (A MOSFET device is thus sometimes referred to in the art as an enhancement mode FET because there is no conduction therethrough until the application of a potential to the gate enhances a channel through which current may flow.)

For a P-channel MOSFET device, a negative voltage must be applied to the gate (relative to the source) in order to turn the switch on. For this reason, P-channel MOSFET devices are very useful in a positive ground system because a negative voltage is readily available to selectively apply to the gate terminal whenever it is desired to turn the switch on. However, for many applications, not only the gate voltage will vary (as controlled in order to turn the switch on and off), but the source voltage may also vary.

Shown in FIG. 3 is a simplified timing diagram illustrating the operation of the P-channel MOSFET switch 36 when a source voltage going first negative and then positive appears at the source while the gate voltage is held open (0 volts). From FIG. 3 it is seen that where both $V_S$ (the source voltage) and $V_G$ (the gate voltage) are at zero volts, the P-channel MOSFET switch remains off. Similarly, with $V_S$ goes negative (to a $-V1$), the device remains off. This is because the gate must be more negative than the source in order for the device to turn on. When $V_S$ goes positive (to $+V2$), and $V_G$ remains at zero volts, the device may turn on. This is effectively the same as applying a negative voltage to the gate—i.e., the gate is more negative than the source. Hence, while $V_S$ is more positive than $V_G$, the switch may be turned on. The switch "may" be turned on because there is associated with every MOSFET device as threshold above which the device is clearly turn on, but below which it may only be partially turned on. In order to assure a very high inpedence between the source and drain—that is, an "off" condition—it is necessary to maintain a zero or negative potential between the source and gate.

Figure 4:
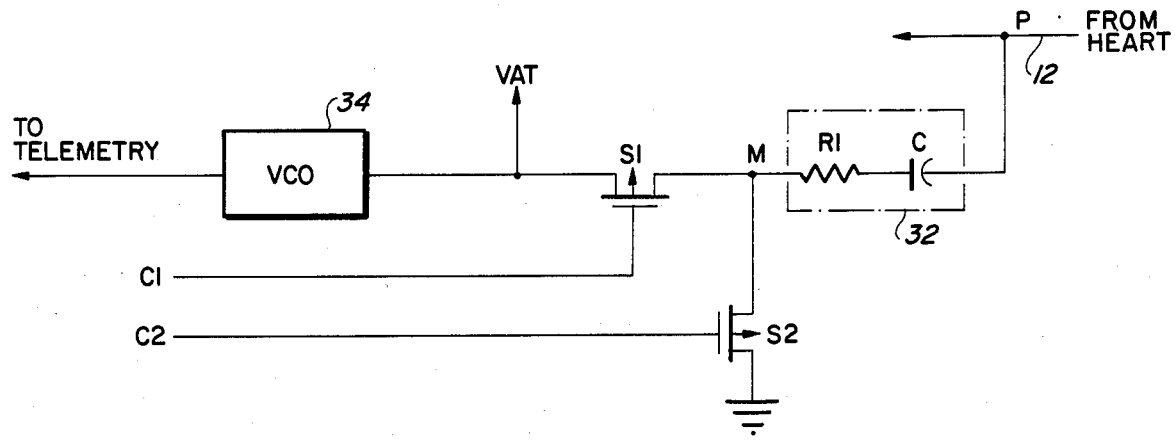
FIG. 4 is a diagram of the present invention implemented with P-channel MOSFET switches.

With the above operation of a P-channel MOSFET switch in mind, reference is now made to FIG. 4 wherein there is shown a partial diagram of a pacemaker as in FIG. 1 wherein the present invention is implemented using P-channel MOSFET devices as switches. In FIG. 4, the sensing/pacing lead 12 is coupled through buffer circuit 32 to monitoring point M as in FIG. 1. (Note, many of the elements of FIG. 1 are not repeated in FIG. 4 for purposes of clarity.) Buffer circuit 32 comprises a resistor R1 and a coupling capacitor C. In the preferred embodiment, the resistor R1 has a value of approximately 100K ohms, and capacitor C has a value of 0.33 microfarads. The point M is coupled to the modulation circuit 34 (a VCO) through switch S1. Switch S1 is a P-channel MOSFET device having its source connected to the point M and its drain connected to the input of the VCO 34. The drain of switch S1 is also designated as VAT, meaning "voltage analog telemetry". The gate of switch S1 is connected to a control signal C1.

The monitoring point M is also connected to a second P-channel MOSFET switch S2. The source of switch S2 is connected to the monitoring point M, and the drain is connected to ground. The gate of switch S2 is connected to a control signal C2.

Figure 5:
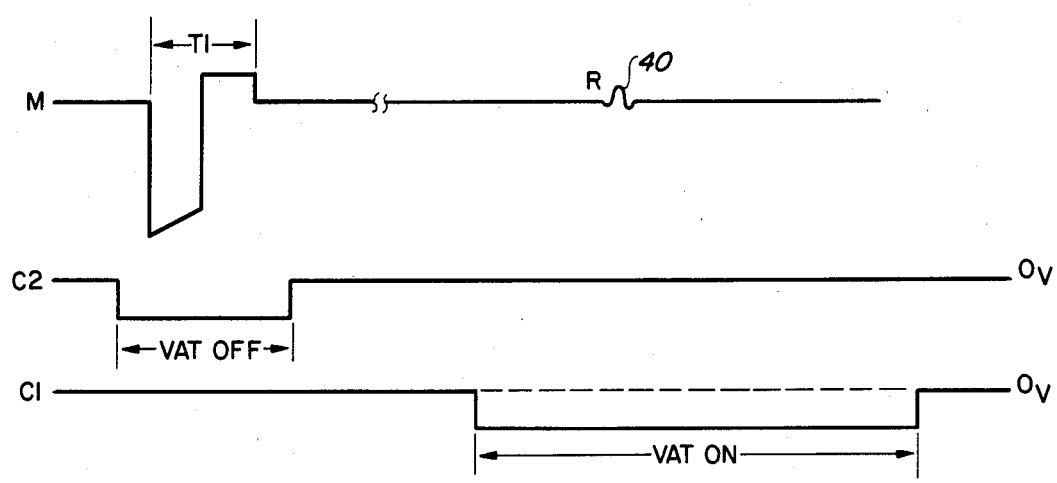
FIG. 5 is a timing diagram illustrating one technique that can be used to control the MOSFET switches of FIG. 4.

One manner of operating the circuit of FIG. 4 is illustrated in the timing diagram of FIG. 5. The top waveform in FIG. 5, labeled M, includes a high level negative and positive excursion occurring during time T1. Inasmuch as the control circuits 22 (FIG. 1) of the pacemaker control when a negative stimulation pulse is generated by the pulse generator 20, it is a simple task to also have the control circuits provide a control signal C2 that turns the voltage analog telemetry (VAT) off during the negative stimulation pulse and for a prescribed time thereafter. Applying such a signal to the gate of S2 assures that point M remains ground during this time. (In this regard, it is noted that the top waveform in FIG. 5, labeled M, is that waveform that would appear at point M if the switch S2 remains open. Obviously, if switch S2 is closed, then point M is grounded and no signal appears thereat.)

When voltage analog telemetry or VAT is desired, at a time other than time T1, then switch S1 is closed with control signal C1. Control signal C1 is generated by the control circuits 22 (FIG. 1) in conventional manner. When switch S1 is closed, and switch S2 is open, any activity appearing at the monitoring point M, such as the sensing of R-wave 40, will be applied to the VCO 34 (modulation circuit) for telemetry to the external transmittor/receiver 28.

As an alternative to generating a control signal C2 as shown in FIG. 5, a suitable detection circuit could be included in the sensing circuits 24 (FIG. 1) in order to determine that portion of T1 during which the waveform is positive. It is only during this positive portion (the latter portion of T1) that switch S2 needs to be turned on, as explained in connection with FIG. 3. Hence, rather than having a control signal C2 that is generated for a fixed time beginning immediately prior to the generation of a stimulation pulse by the control circuits 22, it would be possible to generate a control signal that closes the switch S2 whenever a high level positive signal appears on the sensing/pacing lead 12.

While the invention herein disclosed has been described by means of specific embodiments and applications thereof, numerous modifications and variations could be made thereto by those skilled in the art without departing from the spirit and scope of the present invention. It is therefore to be understood that within the scope of the appended claims, the invention may be practiced otherwise than as specifically described therein.

What is claimed is:

1. In a cardiac pacemaker system comprised of a pacemaker having a pulse generator that generates high level stimulation pulses, a lead connected to said pacemaker through which said pacemaker may deliver high level stimulation pulses to a desired cardiac location and through which low level cardiac signals may be sensed, a receiver remote from said pacemaker, and telemetry means within said pacemaker for transmitting signals applied thereto to said receiver, a means for preserving the integrity of the low level signals comprising:

first switch means for selectively connecting said lead to an input signal line of said telemetry means whenever said high level stimulation pulses are not being delivered over said lead and whenever a telemetry mode is enabled, and for disconnecting said lead from said input signal line whenever said high level stimulation pulses are being delivered over said lead, buffer means interposed between said first switch means and said lead for buffering said telemetry means from signals and stimulation pulses appearing on said lead; and second switch means for selectively connecting the first switch means side of said passive buffer means to a fixed voltage potential within said pacemaker when a high-level signal appears on said lead.

2. The pacemaker of claim 1 further including control circuit means coupled to said pulse generator for generating control signals that control when the pulse generator generates said high level stimulation pulses, and wherein said first and second switch means comprise FET switches that are turned on and off with control signals generated by said control circuit means.

3. The pacemaker of claim 2 wherein said FET switches comprise P-channel FET switches.

4. In an implantable circuit having a pulse generator for generating high level stimulation pulses, a lead connected to said pulse generator for delivering said high level stimulation pulses to a desired tissue location, and a telemetry modulation circuit connected to said lead, said telemetry modulation circuit including means for transmitting to a location remote from said implantable circuit low level signals appearing on said lead, said telemetry modulation circuit having an input signal range limited to low level analog signals, a protection circuit for preventing the high level stimulation signals from appearing at an input terminal of the telemetry modulation circuit, said protection circuit comprising a first semiconductor switch that couples the low level analog signals appearing on said lead to the input terminal of said modulation circuit during selected intervals when said pulse generator is not generating said high level stimulation pulses;

buffer means connected between said lead and said input terminal of said first semiconductor switch; and a second semiconductor switch that connects the first semiconductor switch side of said buffer means to a fixed voltage potential within said implantable circuit whenever said pulse generator is generating said high level stimulation pulses.

5. The protection circuit of claim 4 wherein said first semiconductor switch and said second semiconductor switch comprises P-channel enhancement mode FET transistors.

6. A method for preventing undesirable high level stimulation signals from being applied to an input terminal of a telemetry circuit included within an implantable device, said implantable device having means for generating high level stimulating signals, a lead connected to said generating means and said telemetry circuit through which said high level stimulation signals are selectively delivered and through which low level signals are sensed, said implantable device further having a means for providing power thereto that includes a fixed reference potential, said method comprising the steps of:

(a) buffering a monitoring point connected to said lead with a passive buffer element, both said high level stimulation signals and said low level signals appearing on said lead being detectable at said monitoring point;

(b) switchably connecting the monitoring point of step (a) to said fixed reference potential during the same time that high level stimulation signals appear on said lead; and (c) switchably connecting the monitoring point of step (a) to the input terminal of the telemetry circuit whenever it is desired to telemeter low level signals and whenever said high level stimulation signals are not present on said lead.

* * * * *